United States Patent [19]

Förster et al.

[11] Patent Number: 4,723,985
[45] Date of Patent: Feb. 9, 1988

[54] HERBICIDAL PHENOXYBENZOIC ACID DERIVATIVES

[75] Inventors: Heinz Förster, Wuppertal; Hans-Joachim Santel, Leverkusen; Robert R. Schmidt, Bergisch-Gladbach, all of Fed. Rep. of Germany

[73] Assignee: Bayer Aktiengesellschaft, Leverkusen, Fed. Rep. of Germany

[21] Appl. No.: 925,767

[22] Filed: Oct. 30, 1986

[30] Foreign Application Priority Data

Oct. 31, 1985 [DE] Fed. Rep. of Germany ........ 3538689

[51] Int. Cl.$^4$ .......................... A01N 57/22; C07F 9/40
[52] U.S. Cl. .......................................... 71/86; 558/179
[58] Field of Search ..................... 558/179, 174; 71/86

[56] References Cited

U.S. PATENT DOCUMENTS

| | | | |
|---|---|---|---|
| 4,419,122 | 12/1983 | Swithenbank | 558/179 |
| 4,419,123 | 12/1983 | Swithenbank | 558/179 |
| 4,419,124 | 12/1983 | Swithenbank | 558/179 |
| 4,640,701 | 2/1987 | Diel et al. | 558/179 |

FOREIGN PATENT DOCUMENTS

| | | |
|---|---|---|
| 0165203 | 5/1983 | European Pat. Off. |
| 0078536 | 5/1983 | European Pat. Off. |
| 2311638 | 9/1973 | Fed. Rep. of Germany |

*Primary Examiner*—Anton H. Sutto
*Attorney, Agent, or Firm*—Sprung Horn Kramer & Woods

[57] ABSTRACT

Herbicidally active novel phenoxybenzoic acid derivatives of the formula

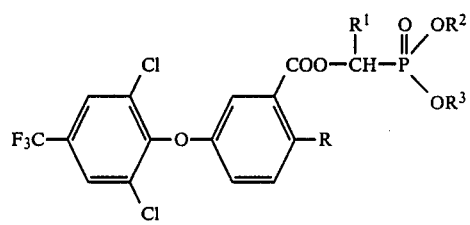

in which
R represents hydrogen, nitro or cyano,
$R^1$ represents hydrogen or alkyl and
$R^2$ and $R^3$ are identical or different and represent hydrogen, alkyl, halogenalkyl or one equivalent of an alkali metal or alkaline earth metal ion, or
$R^2$ and $R^3$ together represent an optionally substituted alkanediyl radical.

9 Claims, No Drawings

HERBICIDAL PHENOXYBENZOIC ACID DERIVATIVES

The invention relates to new phenoxybenzoic acid derivatives, several processes for their preparation and their use as herbicides.

It is already known that numerous phenoxybenzoic acid derivatives have herbicidal properties (compare DE-OS (German Published Specification) No. 2,311,638). Thus, for example, the sodium salt of 3-(2-chloro-4-trifluoromethylphenoxy)-6-nitro-benzoic acid can be used for combating weeds. The action of this substance is good, but some weeds are not always completely combated when low amounts are applied.

New phenoxybenzoic acid derivatives of the formula

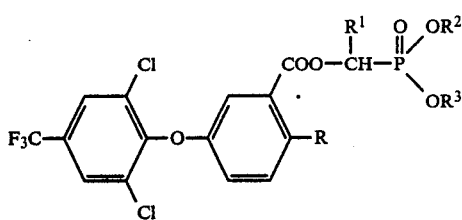

in which
R represents hydrogen, nitro or cyano,
$R^1$ represents hydrogen or alkyl and
$R^2$ and $R^3$ are identical or different and represent hydrogen, alkyl, halogenoalkyl or one equivalent of an alkali metal or alkaline earth metal ion, or
$R^2$ and $R^3$ together represent an optionally substituted alkanediyl radical,
have now been found.

The phenoxybenzoic acid derivatives of the formula (I) contain at least one asymmetrically substituted carbon atom and can therefore exist in various enantiomeric forms. The invention relates both to the possible individual isomers and to mixtures of these isomers.

It has furthermore been found that phenoxybenzoic acid derivatives of the formula (I) are obtained by a process in which (a) phenoxybenzoic acid chlorides of the formula (II)

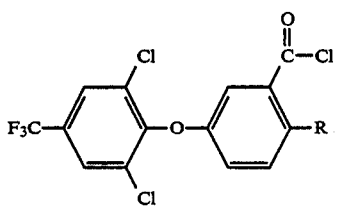

in which R has the abovementioned meaning,
are reacted with hydroxymethylphosphonic acid esters of the formula (III)

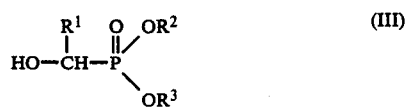

in which $R^1$, $R^2$ and $R^3$ have the abovementioned meanings, if appropriate in the presence of an acid-binding agent and if appropriate in the presence of a diluent, or (b) phenoxybenzoic acid derivatives of the formula (Ia)

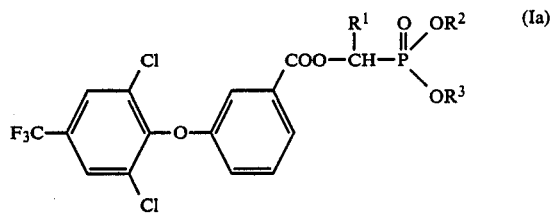

in which $R^1$, $R^2$ and $R^5$ have the abovementioned meanings,
are reacted with a nitrating agent, if appropriate in the presence of a catalyst and if appropriate in the presence of a diluent.

Finally, it has been found that the new phenoxybenzoic acid derivatives of the formula (I) are distinguished by an outstanding herbicidal action.

Surprisingly, the phenoxybenzoic acid derivatives of the formula (I) according to the invention are considerably more effective against some important weeds and have considerably better selective properties than the sodium salt of 3-(2-chloro-4-trifluoromethyl-phenoxy)-6-nitro-benzoic acid, which is a structurally similar, already known active compound with an analogous type of action.

Formula (I) provides a general definition of the phenoxybenzoic acid derivatives according to the invention. Preferred compounds of the formula (I) are those in which
R represents hydrogen, nitro or cyano,
$R^1$ represents hydrogen or alkyl with 1 to 3 carbon atoms and
$R^2$ and $R^3$ are identical or different and represent hydrogen, alkyl with 1 to 6 carbon atoms, halogenoalkyl with 1 to 6 carbon atoms in the alkyl part and 1 to 5 halogen atoms, such as fluorine, chlorine and/or bromine, or one equivalent of a sodium, potassium, calcium or magnesium ion, or
$R^2$ and $R^3$ together represent an alkanediyl radical which has 2 to 5 carbon atoms and is optionally substituted by $C_1$-$C_2$-alkyl.

Particularly preferred compounds of the formula (I) are those in which
R represents nitro,
$R^1$ represents hydrogen or alkyl with 1 or 2 carbon atoms and
$R^2$ and $R^3$ are identical or different and represent hydrogen, alkyl with 1 to 4 carbon atoms, halogenoalkyl with 1 to 4 carbon atoms in the alkyl part and 1 to 3 halogen atoms (fluorine and/or chlorine) or one equivalent of a sodium, potassium or calcium ion, or
$R^2$ and $R_3$ together represent an alkanediyl radical which has 2 or 3 carbon atoms and is optionally substituted by methyl and/or ethyl.

Especially preferred compounds of the formula (I) are those in which
R represents nitro,
$R^1$ represents hydrogen or methyl and
$R^2$ and $R^3$ are identical or different and represent hydrogen, methyl, ethyl, n-propyl, i-propyl, n-butyl, i-butyl, sec.-butyl, tert.-butyl, chloromethyl, chloroethyl, 1-chloro-n-propyl, fluoromethyl, fluoroethyl or 1-fluoro-n-propyl.

The compounds listed by way of their formulae in the following table may be mentioned as examples of phenoxybenzoic acid derivatives of the formula (I):

TABLE 1

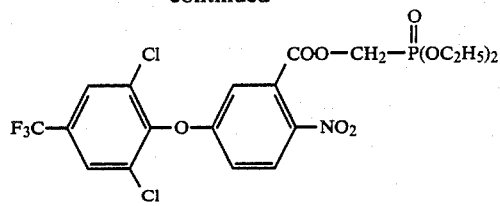

R = H.NO₂

| R¹ | R² | R³ |
|---|---|---|
| H | CH₃ | CH₃ |
| CH₃ | CH₃ | CH₃ |
| H | C₂H₅ | C₂H₅ |
| CH₃ | C₂H₅ | C₂H₅ |
| H | n-C₃H₇ | n-C₃H₇ |
| CH₃ | n-C₃H₇ | n-C₃H₇ |
| H | i-C₃H₇ | i-C₃H₇ |
| CH₃ | i-C₃H₇ | i-C₃H₇ |
| H | n-C₄H₉ | n-C₄H₉ |
| CH₃ | n-C₄H₉ | n-C₄H₉ |
| H | —CH₂—CH₂— | |
| CH₃ | —CH₂—CH₂— | |
| H | —CH₂—CH(CH₃)— | |
| CH₃ | —CH₂—CH(CH₃)— | |
| H | —CH₂—C(CH₃)₂—CH₂— | |
| CH₃ | —CH₂—C(CH₃)₂—CH₂— | |
| H | —CH₂CH₂Cl | —CH₂CH₂Cl |
| CH₃ | —CH₂CH₂Cl | —CH₂CH₂Cl |

If diethyl hydroxymethylphosphonate and 3-(2,6-dichloro-4-trifluoromethyl-phenoxy)-6-nitro-benzoyl chloride are used as starting substances, the course of process (a) according to the invention can be represented by the following equation:

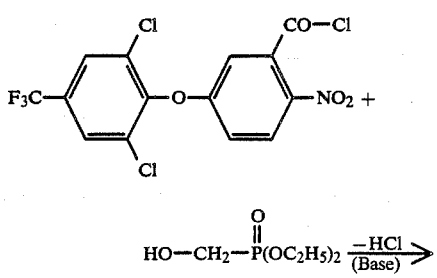

-continued

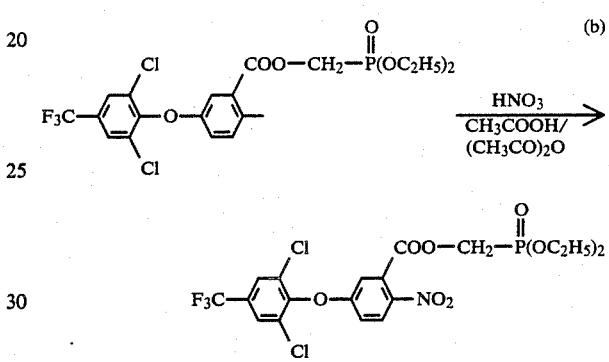

If (diethoxyphosphonyl)methyl 3-(2,6-dichloro-4-trifluoromethylphenoxy)-benzoate is used as the starting substance, nitric acid is used as the reaction component and acetic anhydride and glacial acetic acid are used as diluents, the course of process (b) according to the invention can be represented by the following equation:

Formula (II) provides a definition of the phenoxybenzoic acid chlorides required as starting substances in process (a) according to the invention. In this formula, R preferably has the meaning which has already been mentioned as preferred for this radical in connection with the description of the compounds of the formula (I) according to the invention.

Examples which may be mentioned of the compounds of the formula (II) are: 3-(2,6-dichloro-4-trifluoromethyl-phenoxy)-6-nitro-benzoyl chloride and 3-(2,6-dichloro-4-trifluoromethyl-phenoxy)-benzoyl chloride.

The phenoxybenzoic acid chlorides of the formula (II) are known or can be prepared in a simple manner by known processes (compare DE-OS (German Published Specification) No. 2,311,638 and EP-OS (European Published Specification) No. 63,741).

Formula (III) provides a definition of the hydroxymethylphosphonic acid esters furthermore required as starting substances in process (a) according to the invention. In this formula, R¹, R² and R³ preferably have those meanings which have already been mentioned as preferred for these radicals in connection with the description of the substances of the formula (I) according to the invention.

The compounds of the formula (III) are known and/or can be prepared by generally known methods (compare, for example, Houben-Weyl-Müller "Methoden der organischen Chemie" ("Methods of Organic Chemistry"), Volume 12/1, page 475—Thieme Verlag Stuttgart).

The compounds listed by way of their formulae in the following table may be mentioned as examples of hydroxymethylphosphonic acid esters of the formula (III):

TABLE 2

$$\begin{array}{c} R^1 \quad O \quad OR^2 \\ | \quad \| / \\ HO-CH-P \\ \backslash \\ OR^3 \end{array} \quad (III)$$

| $R^1$ | $R^2$ | $R^3$ |
|---|---|---|
| $CH_3$ | $C_2H_5$ | $C_2H_5$ |
| H | $n\text{-}C_3H_7$ | $n\text{-}C_3H_7$ |
| $CH_3$ | $n\text{-}C_3H_7$ | $n\text{-}C_3H_7$ |
| H | $i\text{-}C_3H_7$ | $i\text{-}C_3H_7$ |
| $CH_3$ | $i\text{-}C_3H_7$ | $i\text{-}C_3H_7$ |
| H | $n\text{-}C_4H_9$ | $n\text{-}C_4H_9$ |
| $CH_3$ | $n\text{-}C_4H_9$ | $n\text{-}C_4H_9$ |
| H | $-CH_2CH_2Cl$ | $-CH_2CH_2Cl$ |
| $CH_3$ | $-CH_2CH_2Cl$ | $-CH_2CH_2Cl$ |
| H | $-CH_2-CH_2-$ | |
| $CH_3$ | $-CH_2-CH_2-$ | |
| H | $-CH_2-CH(CH_3)-$ | |
| $CH_3$ | $-CH_2-CH(CH_3)-$ | |
| H | $-CH_2-C(CH_3)_2-CH_2-$ | |
| $CH_3$ | $-CH_2-C(CH_3)_2-CH_2-$ | |

Process (a) according to the invention for the preparation of the new phenoxybenzoic acid derivatives of the formula (I) is preferably carried out using diluents. Possible diluents here are virtually all the inert organic solvents. These include, preferably, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl and ethyl acetate, nitriles, such as, for example, acetonitrile and propionitrile, amides, such as, for example, dimethylformamide, dimethylacetamide and N-methyl-pyrrolidone, and dimethyl sulphoxide and tetramethylenesulphone.

Acid-binding agents which can be used in process (a) according to the invention are all the acid-binding agents which can usually be employed for such reactions. Preferred possible acid-binding agents are alkali metal hydroxides, such as, for example, sodium hydroxide and potassium hydroxide, alkaline earth metal hydroxides, such as, for example, calcium hydroxide, alkali metal carbonates and alcoholates, such as sodium carbonate and potassium carbonate and sodium methylate or ethylate and potassium methylate or ethylate, and furthermore aliphatic, aromatic or heterocyclic amines, for example triethylamine, trimethylamine, dimethylaniline, dimethylbenzylamine, pyridine, 1,5-diaza-bicyclo-[4.3.0]-non-5-ene (DBN) and 1,8-diazabicyclo-[5.4.0]-undec-7-ene (D8U).

The reaction temperatures can be varied within a substantial range in process (a) according to the invention for the preparation of the phenoxybenzoic acid derivatives of the formula (I). The reaction is in general carried out at temperatures between $-20°$ C. and $+100°$ C., preferably at temperatures between $0°$ C. and $80°$ C.

Process (a) according to the invention is in general carried out under normal pressure. However, it is also possible to carry it out under increased or reduced pressure.

For carrying out process (a) according to the invention, the particular starting substances required are in general employed in approximately equimolar amounts. However, it is also possible for one of the two particular components employed to be used in a larger excess. The reactions are in general carried out in a suitable diluent in the presence of an acid acceptor, and the reaction mixture is stirred at the particular required temperature for several hours. Working up in the process according to the invention is in each case by customary methods.

Formula (Ia) provides a definition of the compounds required as starting substances in process (b) according to the invention. In this formula, $R^1$, $R^2$ and $R^3$ preferably have those meanings which have already been mentioned as preferred for these radicals in connection with the description of the substances of the formula (I) according to the invention.

The compounds of the formula (Ia) are compounds according to the invention and can be prepared by process (a) according to the invention.

In the case of process (b) according to the invention, concentrated nitric acid or heavy metal nitrates, such as, for example, iron(III) nitrate or copper nitrate, are preferably used for nitrating the compounds of the formula (Ia).

Preferred possible catalysts for the nitration to be carried out by process (b) according to the invention are proton acids, such as, for example, sulphuric acid or acetic acid.

Preferred possible diluents for carrying out the nitration by process (b) according to the invention are halogenated hydrocarbons, such as, for example, methylene chloride or 1,2-dichloroethane, and furthermore carboxylic acid anhydrides, such as, for example acetic anhydride.

The reaction temperatures can be varied within a substantial range in the nitration by process (b) according to the invention. The reaction is in general carried out at temperatures between $-20°$ C. and $+60°$ C., preferably between $0°$ C. and $+40°$ C.

The nitration by process (b) according to the invention is in general carried out under normal pressure. However, it is also possible for it to be carried out under increased or reduced pressure.

In carrying out the nitration by process (b) according to the invention, in general 1 to 5 moles, preferably 1.1 to 3 moles, of nitrating agent and, if appropriate, about the same amount of a catalyst are employed per mole of a compound of the formula (Ia). The starting components are preferably brought together while cooling with ice and then stirred until the reaction has ended, if appropriate at a slightly elevated temperature.

Working up is carried out by customary methods. In general, a procedure is followed in which, when the reaction has ended, the reaction mixture is poured into ice-water and filtered with suction or extracted and, if appropriate, the product obtained is purified by recrystallization.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotina, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena; Cyperus, Sorghum, Agropyron, Cynodon, Monochoria, Fimbristylis, Sagittaria, Eleocharis, Scirpus, Paspalum, Ischaemum, Sphenoclea, Datyloctenium, Agrostis, Alopecurus and Apera.

Monocotyledon cultures of the genera: Oryzea, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention are very particularly suitable for selectively combating dicotyledon weeds in monocotyledon and dicotyledon crops, particularly in grain, such as, for example wheat, and in soy beans, by the post-emergence method.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymer substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol esters, for example alkylaryl polyglycol ethers, alkylsulphonates, alkylsulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as naturally occurring phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Known herbicides, such as, for example, N-(2-benzothiazolyl)-N,N'-dimethylurea, 3-(3-chloro-4-methylphenyl)-1,1-dimethylurea, 3-(4-isopropylphenyl)-1,1-dimethylurea, 2-chloro-N-{[4-methoxy-6-methyl-1,3,5-triazin-2-yl)-amino]-carbonyl}-benzenesulphonamide, ethyl 2-{[(4-chloro-6-methoxy-2-pyrimidinyl)-aminocarbonyl]aminosulphonyl}-benzoate, 2-ethylamino-6-(1,1-dimethylethylamino)-4-methylthio-1,3,5-triazine, 4-amino-6-(1,1-dimethylethyl)-3-methylthio-1,2,4-triazin-5(4H)-one, 4-amino-6-(1,1-dimethylethyl)-3-ethylthio-1,2,4-triazin-5(4H)-one, 1-amino-6-ethylthio-3-(2,2-dimethylpropyl)-1,3,5-triazin-2,4-(1H,3H)-dione, 5-(2-chloro-4-trifluoromethyl-phenoxy)-N-methylsulphonyl-2-nitrobenzamide, 2-ethoxy-1- methyl-2-oxo-ethyl 5-(2-chloro-4-trifluoromethylphenoxy)-2-nitro-benzoate, methyl 2-[4-(2,4-dichlorophenoxy)-phenoxy]-propionate, 2-{4-[(3-chloro-5-trifluoromethyl-2-pyridinyl)oxy]-phenoxy}-propionic acid, the R-enantiomer of (trimethylsilyl)-methyl 2-{4-[(3,5-dichloro-2-pyridinyl)oxy]-phenoxy}-propionate, 2,4-dichlorophenoxyacetic acid, 2-(2,4-dichlorophenoxy)-propionic acid, 4-chloro-2-methyl-phenoxy-acetic acid, 2-(4-chloro-2-methylphenoxy)-propionic acid, 3,5-diiodo-4-hydroxy-benzonitrile, 3,5-dibromo-4-hydroxy-benzonitrile, 2-[5-methyl-5-(1-methylethyl)-4-oxo-2-imidazolin-2-yl]-3-pyridinecarboxylic acid, 2-(1-ethoxyamino-butylidene)-5-(2-ethylthiopropyl)-1,3-cyclohexanedione, [(4-amino-3,5-dichloro-6-fluoro-2-pyridinyl)oxy]-acetic acid and 3-isopropyl-2,1,3-benzothiadiazin-4-one 2,2-dioxide, can be used for the mixtures. Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

Example 1

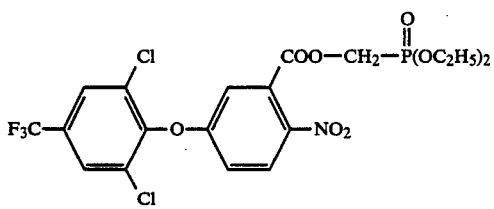

(Process (a))

467 g (2.65 moles) of diethyl hydroxymethanephosphonate and 240 g (3.00 moles) of pyridine are dissolved in 1500 ml of methylene chloride, and a solution of 815 g (1.9 moles) of 2-nitro-5-(2,6-dichloro-4-trifluoromethylphenoxy)-benzoyl chloride in 2000 ml of methylene chloride is added dropwise at −5° C. The reaction mixture is then subsequently stirred at 20° C. for 5 hours. For working up, the organic phase is extracted in each case once with 1000 ml of 2N hydrochloric acid and 1000 ml of saturated sodium bicarbonate solution. The organic phase is then dried over sodium sulphate and concentrated. For purification, the solid substance which remains is stirred with ligroin and filtered off with suction.

605 g (59% of theory) of diethoxyphosphonyl methyl 3-(2,6-dichloro-4-trifluoromethyl-phenoxy)-6-nitrobenzoate of melting point 50°–53° C. are obtained.

The following compounds of the formula (I) can be obtained analogously to Example 1:

TABLE 3

Structure (I):
F$_3$C-phenyl(Cl,Cl)-O-phenyl(R)-COO-CH(R$^1$)-P(=O)(OR$^2$)(OR$^3$)

| Example Number | R | R$^1$ | R$^2$ | R$^3$ | Physical constants |
|---|---|---|---|---|---|
| 2 | NO$_2$ | CH$_3$ | C$_2$H$_5$ | C$_2$H$_5$ | $n_D^{20}$: 1.5233 |
| 3 | NO$_2$ | H | CH$_2$CH$_2$Cl | CH$_2$CH$_2$Cl | |
| 4 | NO$_2$ | H | | —CH$_2$—CH(CH$_3$)— | |
| 5 | NO$_2$ | H | | —CH$_2$—C(CH$_3$)$_2$—CH$_2$— | |

Example A

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0%=no action (like untreated control)
100%=total destruction

In this test, the active compounds according to Examples 1 and 2 exhibit a better selective herbicidal activity and a better tolerance than the comparison substance A (sodium salt of 3-(2-chloro-4-trifluoromethylphenoxy)-6-nitro-benzoic acid) from DE OS (German Published Specification) No. 2,311,638, supra in combating Abutilon, Ipomoea, Sida and Viola in wheat and soy beans.

It is understood that the specification and examples are illustrative but not limitative of the present invention and that other embodiments within the spirit and scope of the invention will suggest themselves to those skilled in the art.

We claim:

1. A phenoxybenzoic acid derivative of the formula

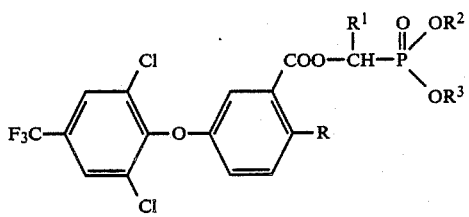

in which
R represents hydrogen, nitro or cyano,
R¹ represents hydrogen or alkyl and
R² and R³ are identical or different and represent hydrogen, alkyl, halogenoalkyl or one equivalent of an alkali metal or alkaline earth metal ion, or
R² and R³ together represent an optionally substituted alkanediyl radical.

2. A method of combating unwanted vegetation which comprises applying to such vegetation or to a locus from which it is desired to exclude such vegetation a herbicidally effective amount of a compound according to claim 1 and a diluent.

3. A phenoxybenzoic acid derivative according to claim 1, in which
R represents hydrogen, nitro or cyano,
R¹ represents hydrogen or alkyl with 1 to 3 carbon atoms and
R² and R³ are identical or different and represent hydrogen, alkyl with 1 to 6 carbon atoms, halogenoalkyl with 1 to 6 carbon atoms in the alkyl part and 1 to 5 halogen atoms, or one equivalent of a sodium, potassium, calcium or magnesium ion or,
R² and R³ together represent an alkanediyl radical which has 2 to 5 carbon atoms and is optionally substituted by $C_1$-$C_2$-alkyl.

4. A phenoxybenzoic acid derivative according to claim 1, in which
R represents nitro,
R¹ represents hydrogen or alkyl with 1 or 2 carbon atoms and
R² and R³ are identical or different and represent hydrogen, alkyl with 1 to 4 carbon atoms, halogenoalkyl with 1 to 4 carbon atoms in the alkyl part and 1 to 3 fluorine and/or chlorine atoms, or one equivalent of a sodium, potassium or calcium ion, or R² and R³ together represent an alkanediyl radical which has 2 or 3 carbon atoms and is optionally substituted by methyl and/or ethyl.

5. A phenoxybenzoic acid derivative according to claim 1, in which
R represents nitro,
R¹ represents hydrogen or methyl and
R² and R³ are identical or different and represent hydrogen, methyl, ethyl, n-propyl, i-propyl, n-butyl, i-butyl, sec.-butyl, tert.-butyl, chloromethyl, chloroethyl, 1-chloro-n-propyl, fluoromethyl, fluoroethyl or 1-fluoro-n-propyl.

6. A compound according to claim 1, wherein such compound is diethoxyphosphonyl-methyl 3-(2,6-dichloro-4-trifluoromethyl-phenoxy)-6-nitro-benzoate of the formula

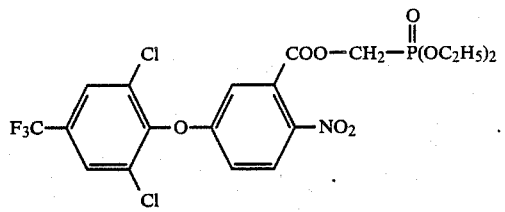

7. A compound according to claim 1, wherein such compound is 1-(diethoxyphosphonyl)-ethyl 3-(2,6-dichloro-4-trifluoromethyl-phenoxy)-6-nitro-benzoate of the formula

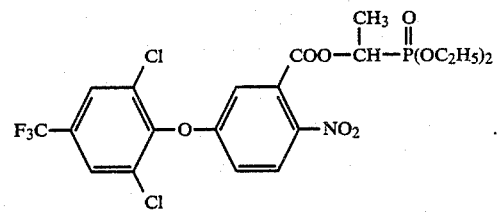

8. A herbicidal composition which comprises a herbicidally effective amount of a compound according to claim 1 and a diluent.

9. The method according to claim 2 wherein such compound is
diethoxyphosphonyl-methyl 3-(2,6-dichloro-4-trifluoromethyl-phenoxy-6-nitro-benzoate or
1-(diethoxyphosphonyl)-ethyl 3-(2,6-dichloro-4-trifluoromethyl-phenoxy)-6-nitro-benzoate.

* * * * *